United States Patent
Gao

(10) Patent No.: US 8,127,454 B1
(45) Date of Patent: Mar. 6, 2012

(54) ROD CUTTER

(75) Inventor: Hua Gao, Fox Point, WI (US)

(73) Assignee: Bradshaw Medical, Inc., Kenosha, WI (US)

( * ) Notice: Subject to any disclaimer, the term of this patent is extended or adjusted under 35 U.S.C. 154(b) by 582 days.

(21) Appl. No.: 12/150,285

(22) Filed: Apr. 28, 2008

(51) Int. Cl.
*B26B 13/00* (2006.01)

(52) U.S. Cl. .................. 30/92; 83/196; 33/630; 33/783; 33/806; 33/809; 606/102

(58) Field of Classification Search ............... 30/92, 94, 30/95, 109; 83/13, 199, 196, 694; 606/1, 606/172, 174, 86 R, 79, 102; 33/783, 787, 33/806, 809, 810, 832, 833, 630
See application file for complete search history.

(56) References Cited

U.S. PATENT DOCUMENTS

| | | | |
|---|---|---|---|
| 54,570 A | 5/1866 | Flinn | |
| 2,323,298 A * | 7/1943 | Cook | 266/70 |
| 3,315,669 A | 4/1967 | Rhodes | |
| 4,581,958 A | 4/1986 | Shull | |
| 5,261,303 A | 11/1993 | Strippgen | |
| 5,285,702 A | 2/1994 | Hillinger | |
| 5,404,616 A | 4/1995 | Carmien | |
| 5,515,574 A | 5/1996 | Larson | |
| 5,836,937 A | 11/1998 | Holmes | |
| 5,988,027 A | 11/1999 | Lenox | |
| 6,058,820 A | 5/2000 | Rinner | |
| 6,238,292 B1 * | 5/2001 | Pelkey | 463/47.7 |

* cited by examiner

*Primary Examiner* — Phong Nguyen
(74) *Attorney, Agent, or Firm* — Absolute Technology Law Group, LLC

(57) ABSTRACT

A rod cutter and method of measuring rod length and then cutting, and including two telescoping handles operable with only longitudinal force on the handles. The cutting precision is effective by a gauge that aligns with the cutting line on the rod and then positions the rod in the cutter according to that alignment. Storage for the gauge is provided on the cutter.

8 Claims, 8 Drawing Sheets

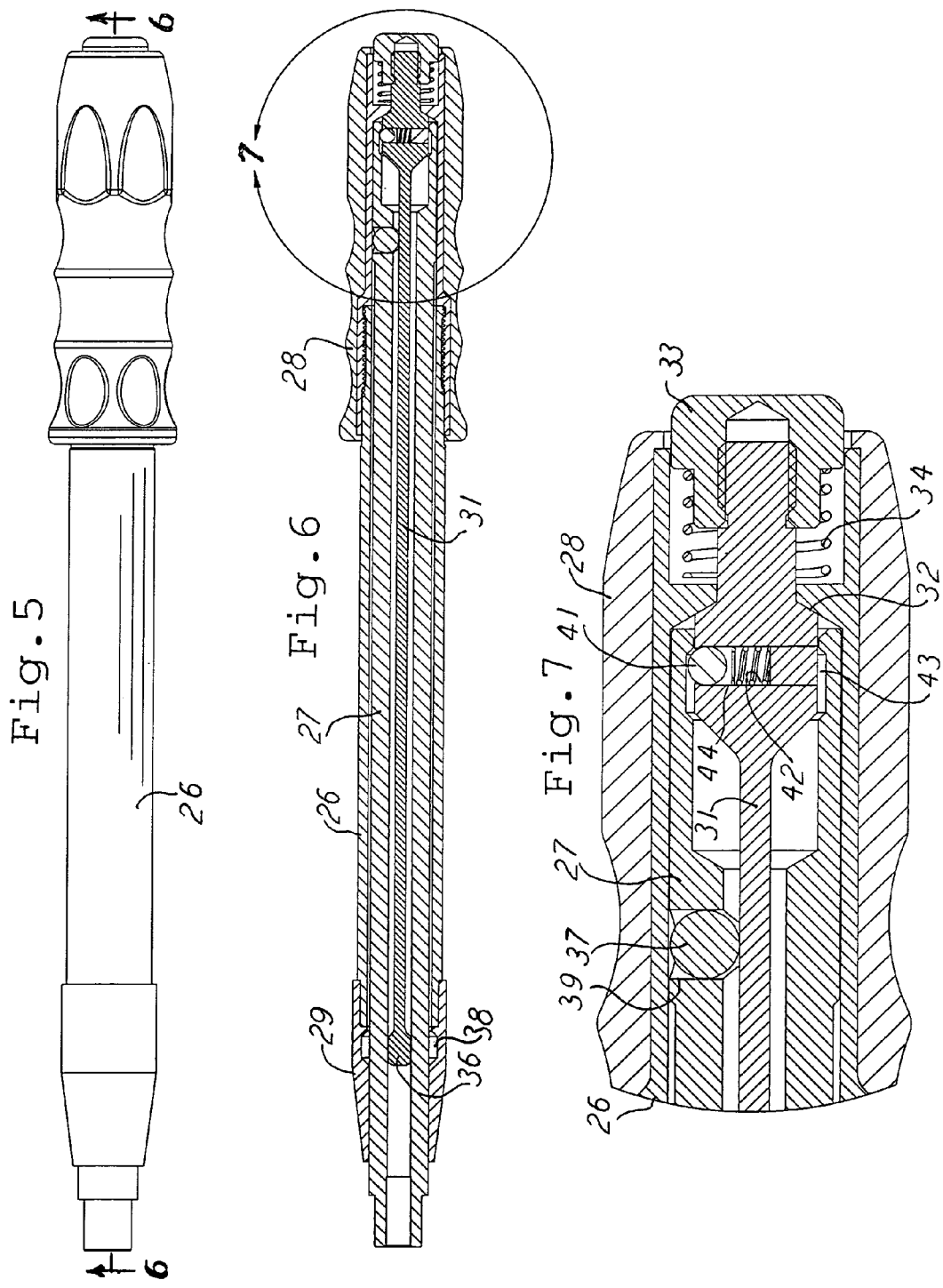

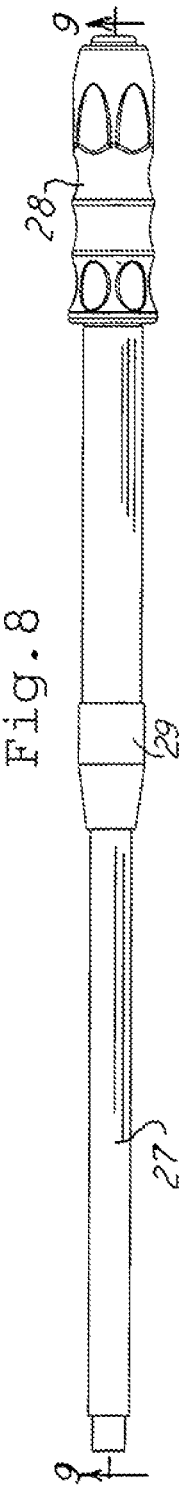
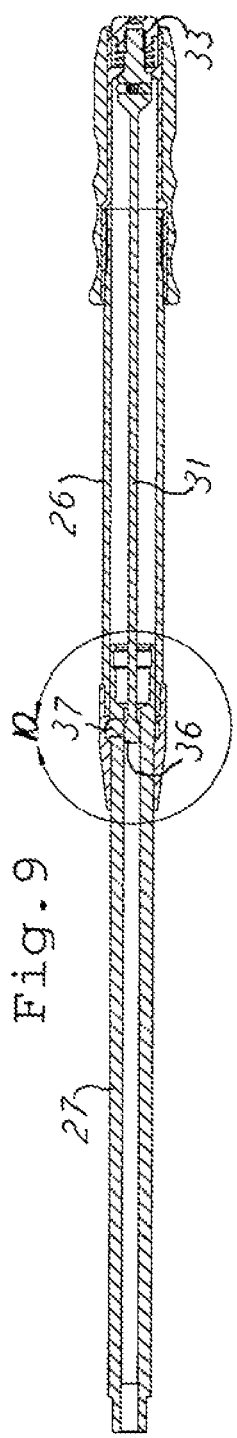
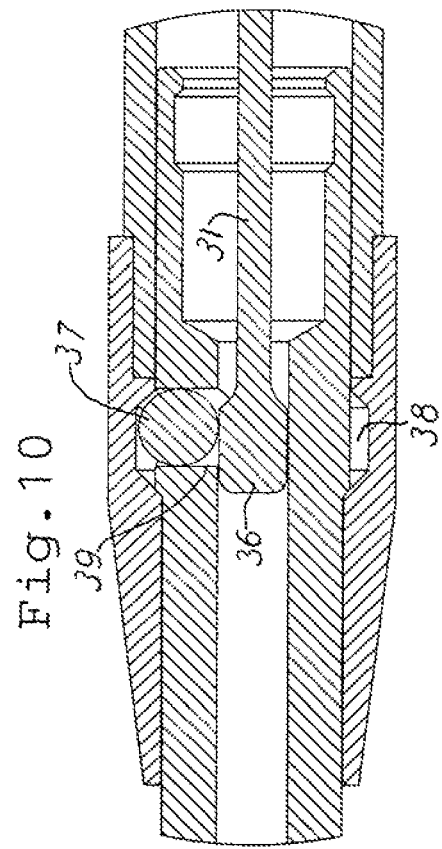
Fig. 8
Fig. 9
Fig. 10

ROD CUTTER

This invention relates to a rod cutter and method, such as those which are used to cut rods for human medical uses such as attachment to a patient's spine.

BACKGROUND OF THE INVENTION

Metal rods are employed to stabilize a patient's spine when suitably attached to the spine. Fasteners are attached to the spine and the rod can be attached to the fasteners to span a vertebrae or two and thereby support the spanned vertebrae. It is important the rods be of precise lengths for the patient and the spanned vertebrae.

Heretofore, rod cutters enclosed the rod to be cut and then the precise location of the rod in the cutter was not known. Thus the precise length of the cut was not readily and easily known.

Also, previous rod cutters have only a fixed handle length, so only one torque arm is available on those cutters, and thus there is only limited cutting force. If a heavy rod were to be cut, the length of the cutter arms might not produce sufficient torque, at least not for all users with different arm strengths.

This invention also provides for measuring and detecting the precise length of rod cutting and for lengthening the handles for necessary cutting torque. This is accomplished in an easily adjustable cutter arrangement and method. The handle can be lengthened with only a axial pull thereon, though it is releasably secured in a set length prior and after the lengthening pull.

Further, the precision for cutting the rod to a required length is accomplished by a ready and easily applied structure and method.

BRIEF DESCRIPTION OF THE DRAWINGS

FIG. 5 is a side elevation view of one handle of the rod cutter.

FIG. 6 is a section view taken along a plane designated by the line 6-6 on FIG. 5.

FIG. 7 is an enlarged section view of a portion designated A on FIG. 6.

FIG. 8 is a side elevation view of an interior portion of the rod cutter handle.

FIG. 9 is a section view taken along a plane designated by the line 9-9 on FIG. 8.

FIG. 10 is an enlarged section view of a portion designated B on FIG. 9.

DETAILED DESCRIPTION OF A PREFERRED EMBODIMENT AND METHOD

Figure 3:
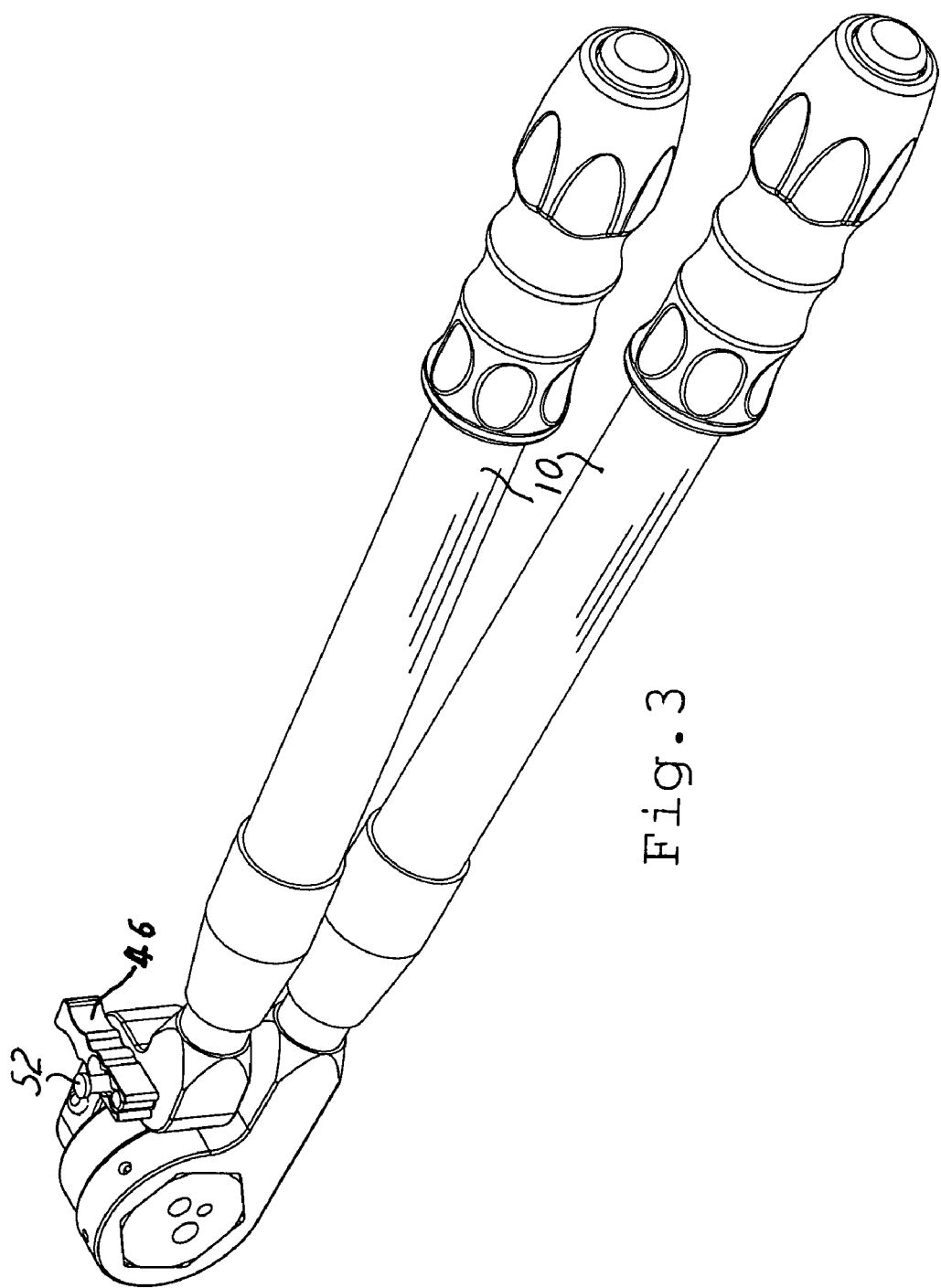
FIG. 3 is a side perspective view similar to FIG. 1 but with two parts added thereto.
Figure 4:
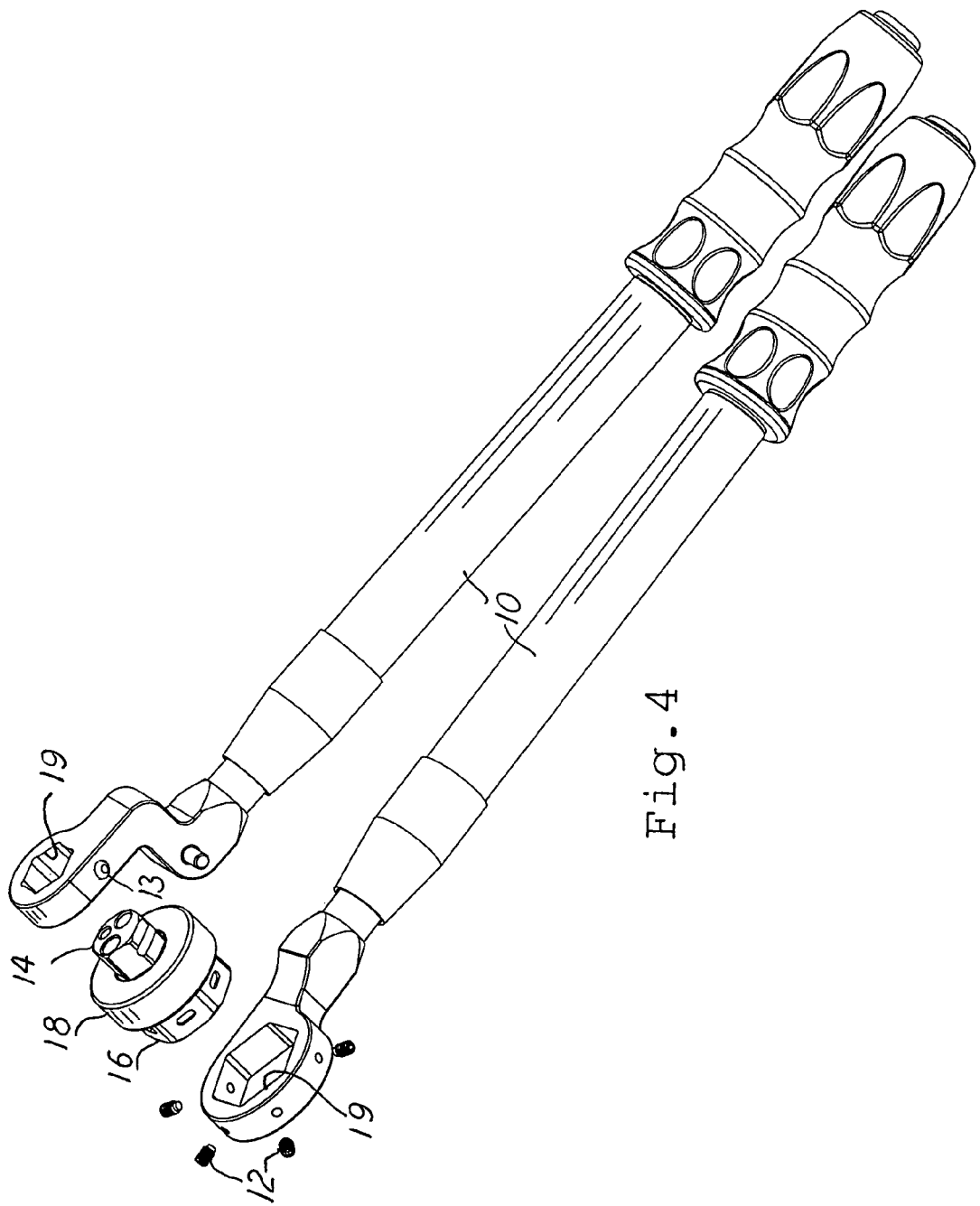
FIG. 4 is a top perspective view of the rod cutter in exploded display.

FIGS. 1-4 show the full views of the rod cutter of this invention. It includes two identical telescopic handles 10 which can extend and contract in response to only longitudinal forces on the handles, that is pull and push forces along the handles longitudinal axes A. Each handle 10 attaches to the cutter head 11 which has the usual two moving portions for severing a rod placed in the head, in the usual manner. FIG. 4 shows the disassembled parts which are otherwise connected together by screws 12 and 13, again in manner to have the screws 12 enter shown slots on the piece 16. The cutter head 11 has its two relatively rotatable parts 14 and 16 which together present the rod cutting edges at 17. A cap 18 axially holds the cutter parts together.

The respective handles 10 have hexagonal openings at 19 for rotationally engaging the cutter head parts 14 and 16 upon scissors action of moving the handles 10, in the usual manner.

Figure 1:
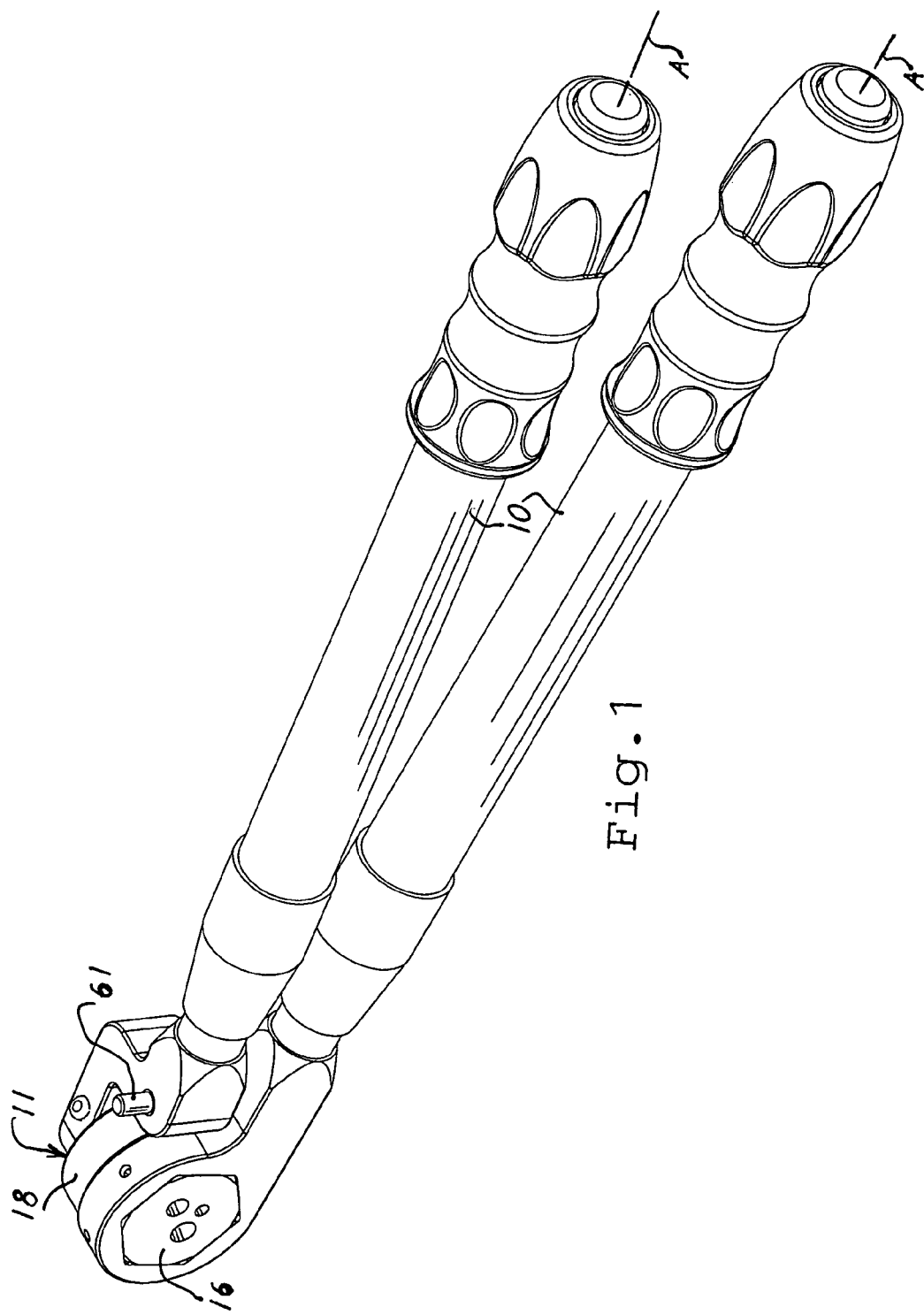
FIG. 1 is a side perspective view of a rod cutter of this invention.
Figure 2:
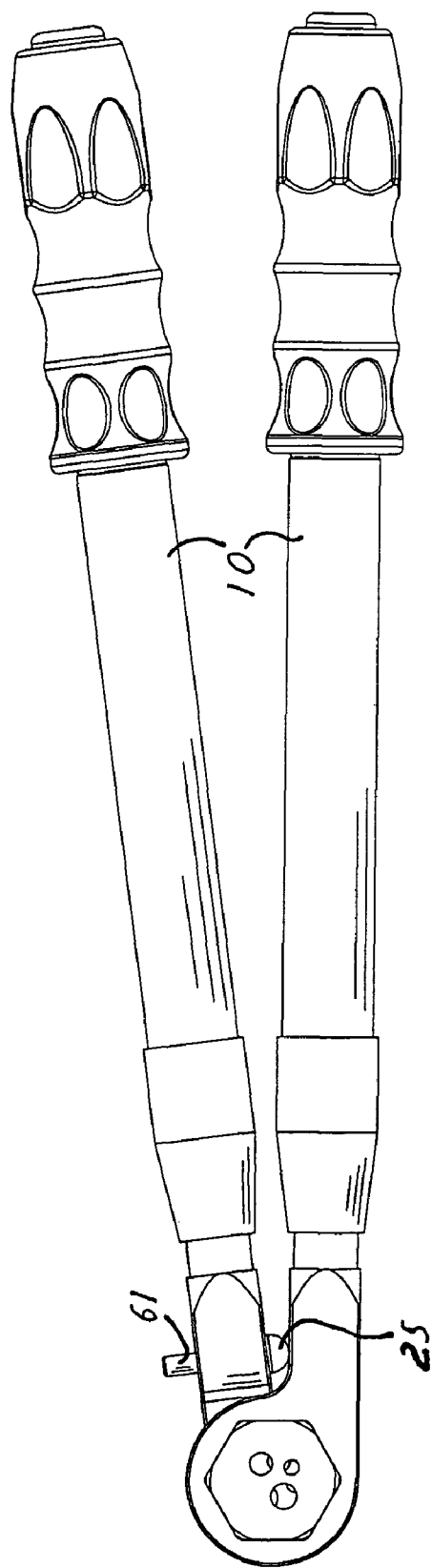
FIG. 2 is a side elevation view of the rod cutter.
Figure 13:
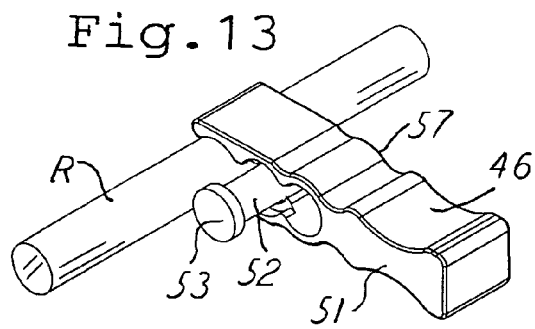
FIG. 13 is a side perspective view of the part shown in FIG. 11 with a part and also the rod to be cut added thereto.
Figure 14:
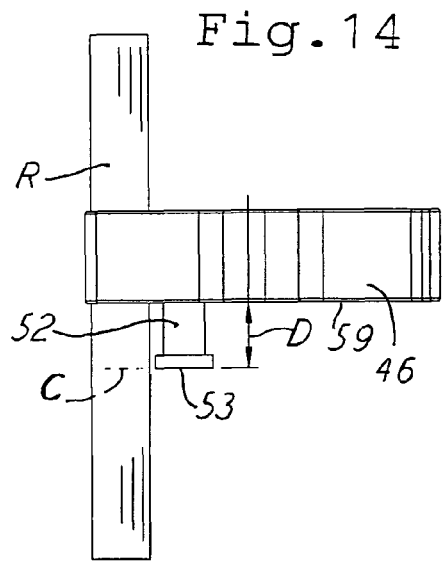
FIG. 14 is a top plan view of FIG. 13.
Figure 18:
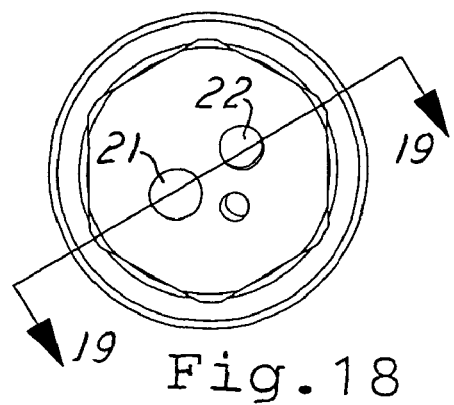
FIG. 18 is a left end elevation view of the rod cutter seen in FIG. 17.
Figure 19:
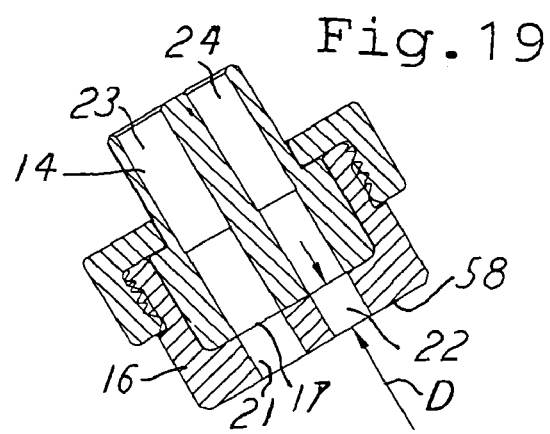
FIG. 19 is a section view taken along a plane designated 19-19 on FIG. 18.

Of course, when the handles are pivoted close to each other, as in the drawings 1-3, the cutters 14 and 16 have their respective FIG. 19 shown rod receiving holes 21, 22, 23, and 24 aligned to axial receive a rod such as that shown in FIGS. 13 and 14. There are actually three different size diameter holes, such as seen in FIG. 1, all for different rod diameters. The cutting edges 17 align with each other at each of the three holes when the handles are in the together position of FIG. 2 and a stop 25 establishes that alignment in serving as a stop for the together pivoting action of handles 10.

To effect the telescopic action of the handles 10, the arrangement is such that the handles can be longitudinally extended and longitudinally contracted with only longitudinal force on the handles. However, the handles are releasably secured in both of those adjusted positions which are overcome with sufficient longitudinal force on the handles.

To accomplish the above, see FIGS. 5 and 6 showing a handle 10 without the cutter head. Each handle 10 includes an outer sleeve 26 and a hollow shaft 27 in telescopic relationship. There is also a hand grip 28 attached to the sleeve 26 and a collar 29 is attached to the sleeve 26 and is slidable on the shaft 27. Thus the two parts 26 and 27 are arranged to telescope between the relationship of FIG. 6 and FIG. 9.

FIG. 7 shows there is an inner shaft 31, and the shafts 27 and 31 axially abut at 32 and there is a button 33 and a spring connection 34 thereby establish an axial together relationship to be axially movable together. Shaft 31 has the button 33 fixed thereon, and the compression spring 34 forces the shaft 31 rightward so the abutment limits the relative movement of the sleeve 26 and shaft 31 rightward, but the spring 34 permits leftward movement of the shaft 31 relative to the sleeve 26. Therefore, upon axial extension of the handle, the sleeve 26 moves rightward and the shaft 27 remains fixed. Through the spring 34 and the button 33, the inner shaft 31 also moves rightward and that movement continues until the enlargement 36 on the shaft 31 arrives at the position of FIGS. 9 and 10 to thereby force a detent or ball 37 into a circular recess 38 in the collar 29 on the outer shaft 27. The ball 37 is carried on the shaft 27 in a radial opening 39 for radial movement but limited outer radial movement. In that manner, the sleeve 26 and shaft 27 are axially fixed by the detent 37 but are releasable upon axial force on the handle parts to move the enlargement 36 off the ball 37, when desired to contract the handle. There is no requirement of maneuvering any other part to effect that axial release, only the axial force on the handle parts is required.

While the detent 37 is in the FIG. 10 position, it is in contact with both the sleeve collar 29 and the shaft 27 to thereby restrict relative longitudinal movement between the two. Inward force on the button 33 moves the shaft 31 axially to move the enlargement 36 off the ball 37 and thereby release the ball 37 from holding the outer sleeve 26 and thus effect contraction between the handle parts. So only axial force is required for the telescopic action of contraction.

In the contracted mode, a ball detent 41 is restricted radially inwardly in a radial hole 42 in the inner shaft 31, and it can be engaged in a circular groove 43 in the shaft 27 to releasably hold the two telescoping parts together longitudinally. A spring 44 urges the ball 41 into the groove 43. With that arrangement, the handle parts are releasably held in the telescopically contracted mode and only an axial force is required to overcome the holding force for the extension. So the two detents releasably hold the telescoping parts in their two modes, and only axial forte is required for changing the modes. That is the method of operation.

FIGS. 11-16 show a clip 46 which can be slightly flexible and which has two legs 47 flexibly movable toward and away from each other and it has two part-circular passageways 48 and 49 therethrough. FIGS. 13 and 14 show that a rod R is held in the opening 48 and extends perpendicular to the main extent of the clip holder 46. So the clip has a width along the length of the rod R and it can be precisely positioned along the rod R. The clip flexibility renders it firm on the rod R and precisely aligned therewith, as seen in FIGS. 13, 14, and 17.

The clip 46 also has a grip portion 51 for the operator to hold and position the clip which is a gauge for guiding the cutting of the rod R. The flexibility of the clip legs 47 is such that the legs snugly grip on the rod R according to the unique diameter of the rod R, and the clip can be slid along the rod, as desired.

Figure 16:
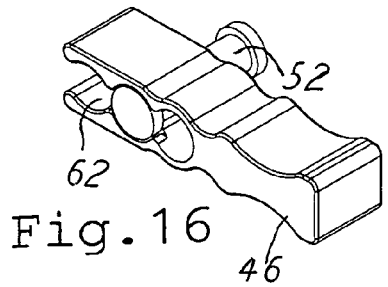
FIG. 16 is a side perspective view of the two parts of FIG. 13, in altered positions.
Figure 12:
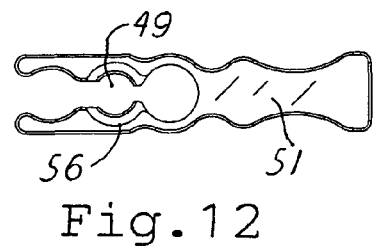
FIG. 12 is a side elevation view of the part shown in FIG. 11.
Figure 15:
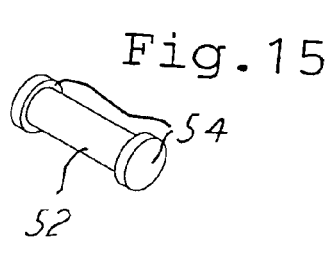
FIG. 15 is a side perspective view of the part in the assembly shown in FIG. 13.
Figure 11:
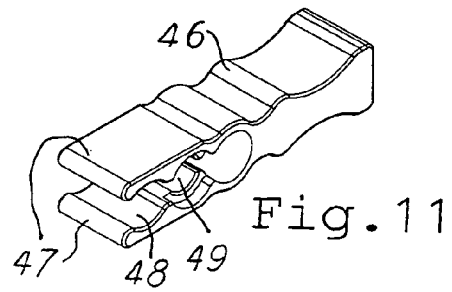
FIG. 11 is a side perspective view of a part shown in FIG. 3.
Figure 17:
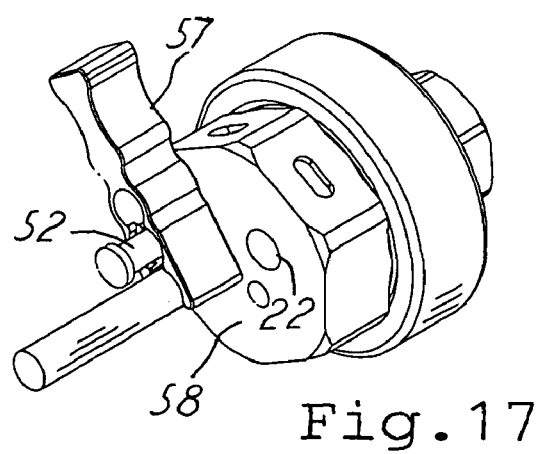
FIG. 17 is a perspective view of an interior portion of FIG. 1 with the parts of FIG. 13 added thereto in rod cutting ready position.

FIG. 14 shows a cutting line C on the rod R, and a gauge in the form of a cylindrical pin 52 is in the opening 49 in the clip and it can slide along its axis relative to the clip 46, such as between the FIG. 13 and FIG. 16 positions. In the position shown in FIGS. 13 and 14, it can be said that the pin is fully inserted into the clip 46, and it is extended, and its outer face 53 aligns with the proposed cutting line C. The pin 52 has flanged ends 54, and the clip 46 has countersunk holes 56 on both sides thereof for receiving the flanges 54 to have the pin flush with the face 57 of the clip in the initial positions. Thus, when the rod R, with the clip 46 thereon, is inserted into the cutter head, as shown in FIG. 17, the clip face 57 is in flat contact with the cutter head face 58 and thereby the pin 52 is slid to the left and extends as seen in FIG. 17.

The arrangement is such that the distance D from the cutter head wall 58 to the cutters 17 is the same as the distance D from the clip wall 59 to the pin surface 53. So that provides for the pin 52 to slid away from the cutter head while inserting the rod. The FIG. 14 extended length of the pin 52 is arranged that way. That means upon insertion of the rod into the cutter that the cutting line C is placed exactly in line with the cutting edges 17 for the desired precise cutting of the length of the rod R.

FIGS. 1 and 3 show a mounting post 61 on the cuter head for receiving the flexible clip 46 in the shown storage mode. So the clip opening 48 is available for snapping the clip onto the post 61.

The inventive method is heretofore described in conjunction with the construction. There are the three diametrical sizes for the rods of those diameters. The handles can be extended and contracted with only longitudinal force thereon, and they are releasably held in telescoped relationships by the detents, until overcome by the axial forces mentioned. The method of the precise length cutting is also described in the foregoing.

So the required preferred embodiments of both the apparatus and methods are disclosed, and the scope of the invention should be determined by the verbal extent of the claims.

What is claimed is:

1. A surgical rod cutter comprising:
   two pivotally attached handles and a cutter head for severing a rod, said cutter head having openings of different diameters for receiving rods of different diameters and thereby requiring cutting forces of different amounts,
   each of said handles having two telescoping members extending along a longitudinal axis for extension and contraction between said members,
   a first detent interengageable between said two telescoping members for releasably securing said two telescoping members in relative telescopic extended relationship and a second detent interengageable between said two telescoping members for releasably securing said two telescoping members in relative telescopic contracted relationship,
   both said detents being operable in response to a force along said longitudinal axis, wherein said second detent is releasable in response to a pulling force on said members along said longitudinal axis for the telescopic extension of said members,
   said openings having entries on said head and cutting edges surrounding said openings,
   a detachable cutting edge location indicator mounted on said rod comprising:
      a U-shaped tension clip which partially encloses said surgical rod and exerts pressure on said surgical rod to secure said surgical rod in a position perpendicular to said U-shaped tension clip, said U-shape tension clip further including counter-sunk holes; and
      a cylindrical pin having an inner flanged end and an outer flanged end, wherein said cylindrical pin is positioned so that when an outer surface of said outer flanged end is flush with an outer surface of said U-shaped tension clip, said inner flanged end is visibly positioned to indicate a location of a desired cut on a rod.

2. The surgical rod cutter as claimed in claim 1, wherein a distance between an outer surface of the inner flanged end and an inner surface of the U-shaped tension clip is equal to a distance between the outer surface of the cutting head and the cutting edge.

3. The surgical rod cutter as claimed in claim 1, wherein the flanged ends of the cylindrical pin structurally limit axial movement of the cylindrical pin in the U-shaped tension clip.

4. The surgical rod cutter as claimed in claim 1, wherein a connector is provided on the surgical rod cutter for receiving the detachable cutting edge location indicator in a storage mode.

5. A surgical rod cutter comprising:
   a cutting head with openings for receiving rods to be cut to length, wherein said openings have entries and cutting edges surrounding said openings, and wherein each of said openings has a different diameter;
   two pivotally attached longitudinally telescoping handles, each of said handles comprised of:

a hexagonal opening for rotationally engaging said cutting head;

an outer sleeve and a hollow shaft in telescopic relationship, wherein said hollow shaft contains a radial opening holding a first detent and a groove;

a collar having an inner circular recess and attached to said outer sleeve and slidable on said hollow shaft;

a hand grip attached to said outer sleeve;

an inner shaft with a radial aperture and a second detent contained by said radial aperture;

a button-spring mechanism, wherein said inner shaft axially abuts at said button-spring mechanism; and a spring received in the radial aperture and biasing said second detent against said groove on said hollow shaft when said handles are contracted;

wherein the first detent engages the inner circular recess of the collar to restrict axial movement between the collar and the inner shaft when the handles are extended; and a detachable cutting edge location indicator comprised of:

a U-shaped tension clip which partially encloses a surgical rod and exerts pressure on said surgical rod to secure said surgical rod in a position perpendicular to said U-shaped tension clip, said U-shape tension clip further including counter-sunk holes; and a cylindrical pin having an inner flanged end and an outer flanged end, wherein said cylindrical pin is positioned so that when an outer surface of said outer flanged end is flush with an outer surface of said U-shaped tension clip, said inner flanged end is visibly positioned to indicate a location of a desired cut on a rod.

6. The surgical rod cutter as claimed in claim 5, wherein a distance between an outer surface of the inner flanged end and an inner surface of the U-shaped tension clip is equal to a distance between the outer surface of the cutting head and the cutting edge.

7. The surgical rod cutter as claimed in claim 5, wherein the flanged ends of the cylindrical pin structurally limit axial movement of the cylindrical pin in the U-shaped tension clip.

8. The surgical rod cutter as claimed in claim 5, wherein a connector is provided on the surgical rod cutter for receiving the detachable cutting edge location indicator in a storage mode.

* * * * *